United States Patent
Toh

Patent Number: 5,969,374
Date of Patent: Oct. 19, 1999

[54] CONTRAST MEASUREMENT SYSTEM FOR LASER MARKS

[75] Inventor: Peng Seng Toh, Singapore, Singapore

[73] Assignee: Hewlett-Packard Company, Palo Alto, Calif.

[21] Appl. No.: 09/026,699

[22] Filed: Feb. 20, 1998

[30] Foreign Application Priority Data

Dec. 8, 1997 [SG] Singapore .......................... 9704371.5

[51] Int. Cl.$^6$ .............................. G06K 7/10; G01N 15/06
[52] U.S. Cl. ............................................ 250/566; 250/572
[58] Field of Search ..................................... 356/237, 390, 356/394, 402, 446; 250/559.44, 559.46, 559.39, 559.07, 559.08, 572, 566; 235/375

[56] References Cited

U.S. PATENT DOCUMENTS

| | | | |
|---|---|---|---|
| 4,339,745 | 7/1982 | Barber et al. | 250/566 |
| 4,972,093 | 11/1990 | Cochran et al. | 250/572 |
| 5,585,616 | 12/1996 | Roxby et al. | 250/566 |

*Primary Examiner*—Frank G. Font
*Assistant Examiner*—Roy M. Punnoose

[57] ABSTRACT

This invention relates to a technique of contrast measurement especially useful for the measurement of contrast of laser mark. The technique involves measuring the light intensity coming from a laser mark and the intensity coming from a background on the integrated circuit, calculating the contrast based on the intensities, and comparing to a gray scale. This invention enables contrast to be measured and communicated with respect to a set of references and hence eliminates subjective judgement.

14 Claims, 6 Drawing Sheets

CONTRAST MEASUREMENT SYSTEM FOR LASER MARKS

FIELD OF THE INVENTION

This invention relates to a technique for testing laser marks, and more particularly to an optical technique for testing laser marks.

BACKGROUND

The use of laser for integrated circuit (IC) marking has become very popular mainly due to its flexibility and speed. In comparison to ink marking, laser marking does not need any dispensable medium such as ink. However, one major disadvantage associated with laser marking is its reduction in contrast. Unlike ink marking where inks are printed onto the IC surface, laser marking operates by removing materials from the IC surface and hence creates a groove-like depression. Materials are being burnt away by the striking laser beam. The roughness of the laser marked surface is different from that of the unmarked surface. The contrast generated by laser marking is a result of these two factors: depression and roughness. Another factor that affects the contrast is the remnant of the burnt compound which has a different reflectivity from the original material.

As far as the external factor is concerned, the apparent contrast of the laser mark is very much dependent on the lighting and the viewing geometry. In other words, the direction of the incident light and the viewing direction determine how well the laser mark can be seen. Usually the depth of a laser mark is about few tens of microns and its roughness is rougher than that of the unmarked surface. In general, one would view the IC marking directly from the top. In this case, the lighting must be set to an oblique angle in order to highlight the contrast of the laser mark. If the lighting is cast from a direction more or less the same as the viewing direction, the laser mark can hardly be seen. The entire IC surface will be brightened up instead.

There have been many attempts to improve the contrast of the laser mark. For example, new molding compound which reacts to laser and produces a contrast between the unmarked and marked surface have been experimented. Another example is the use of different surface glazing material from that of the matrix compound. The laser beam removes the surface material and exposes the underlying matrix compound and hence produces a high contrast mark. However, all these attempts have not been able to fully commercialize due to factors such as cost, etc.

DESCRIPTIONS OF THE ACCOMPANIED DRAWINGS

FIG. 1 A cross-sectional view of a laser marked surface.

FIG. 2 A surface reflection model which consists of three components: diffuse lobe, specular lobe and specular highlight.

FIG. 3A Laser mark contrast measurement system configuration.

FIG. 3B Embodiment of a laser mark contrast measurement system according to the present invention.

FIG. 4 A typical image acquisition system flow.

FIG. 5 A laser mark character "B".

FIG. 6 An image of the ANSI traceable KODAK "Gray Scale Card".

SUMMARY

In one aspect, the present invention provides a method and a system for testing laser marks in a manner which reduces the need for subjective judgment.

In an embodiment, a method of testing a laser mark applied to a surface of a semiconductor device includes the steps: illuminating the laser mark to be tested and the adjacent unmarked surface of the semiconductor device; determining the intensity of light reflected from a portion of the laser mark ($I_M$); and evaluating the determined intensity value to assess the acceptability or otherwise of the laser mark.

Preferably, the evaluation step involves determining the intensity of light reflected from a portion of the adjacent unmarked surface ($I_U$) and comparing the value of ($I_M$) with the value ($I_U$) to obtain a value of the contrast between the portion of the laser mark and the portion of the adjacent surface. In a more preferred embodiment, the contrast (Con) is obtained according the equation:

$$\text{Con} = |\text{Log}(I_M) - \text{Log}(I_U)|$$

In the equation, Log represents the logarithmic value. The present invention also provides, in another aspect, an apparatus for testing a laser mark applied to a surface of a semiconductor device. In an embodiment, the apparatus includes a light source for illuminating the laser mark and the adjacent surface of the semiconductor device; image sensor to detect light reflected from a portion of the laser mark and an adjacent portion of the unmarked surface; and a processor to determine a measure of contrast between the portion of the laser mark and the adjacent portion. In a preferred embodiment, the processor calculates the contrast according to the above equation:

$$\text{Con} = |\text{Log}(I_M) - \text{Log}(I_U)|.$$

Using the present technique for inspecting laser marks, laser marks can be consistently determined with high-speed, even in an application for on line inspection.

DETAILED DESCRIPTION OF SPECIFIC EMBODIMENTS OF THE INVENTION

Figure 1:
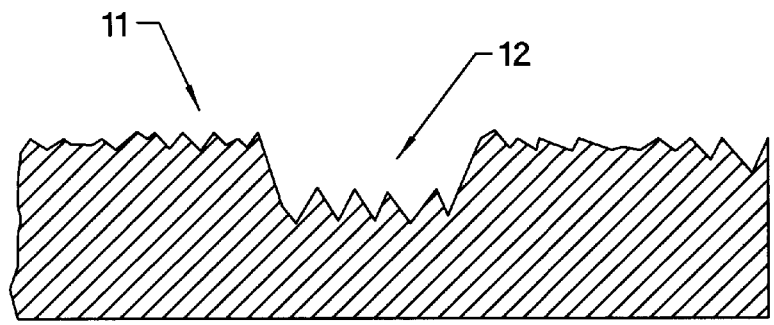
Figure 2:
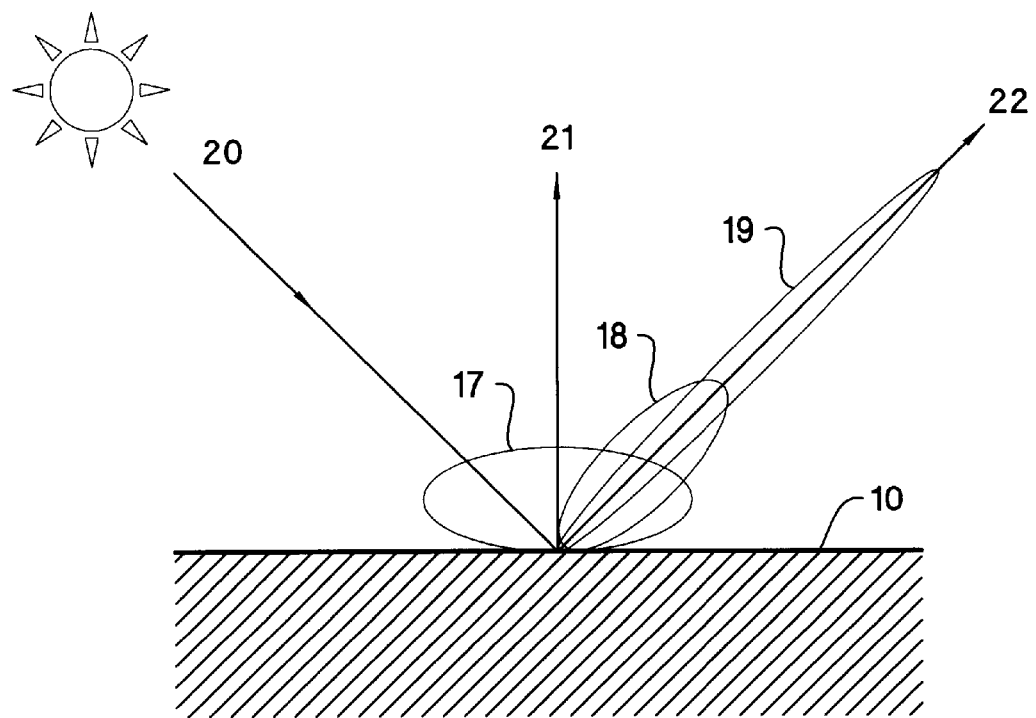

Generally, the reflection produced by a ray of light 20 striking on a surface 10 can be modeled as having three components: diffuse lobe 17 (in the direction of reflection as indicated by an arrow 21), specular lobe 18 and specular highlight 19 (in the direction of reflection as indicated by arrow 22). FIG. 2 illustrates the surface reflection model. The ratio of these three components are largely determined by the roughness of the surface. When a surface is smooth, the diffuse lobe and specular lobe are rather small and the specular highlight dominates. For example, a mirror which has a very smooth surface displays such characteristics. On the other hand, a piece of white paper which is uniformly rough would have small specular highlight but displayed stronger diffuse lobe and certain extent of specular lobe.

In the case of an IC with laser mark, there are two types of surfaces: marked surface and unmarked surface. The laser marked surface is rougher than the unmarked surface. As noted above, a smooth surface exhibits a stronger specular highlight and specular lobe than a rough surface. Since the material remains the same in the marked and unmarked surfaces, the surface have the same albedo, which can hence be ignored in the following description.

Figure 3A:
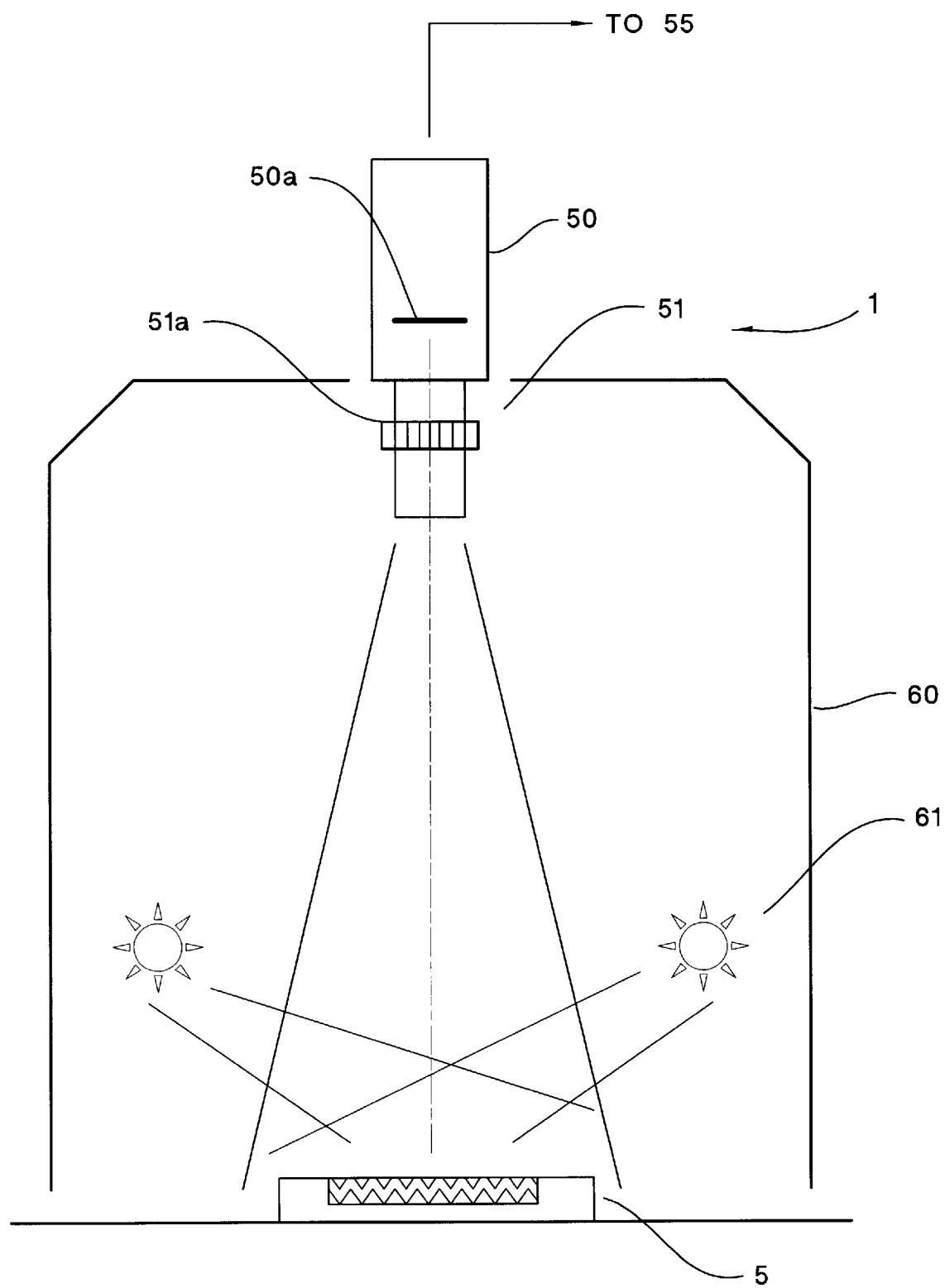
Figure 3B:
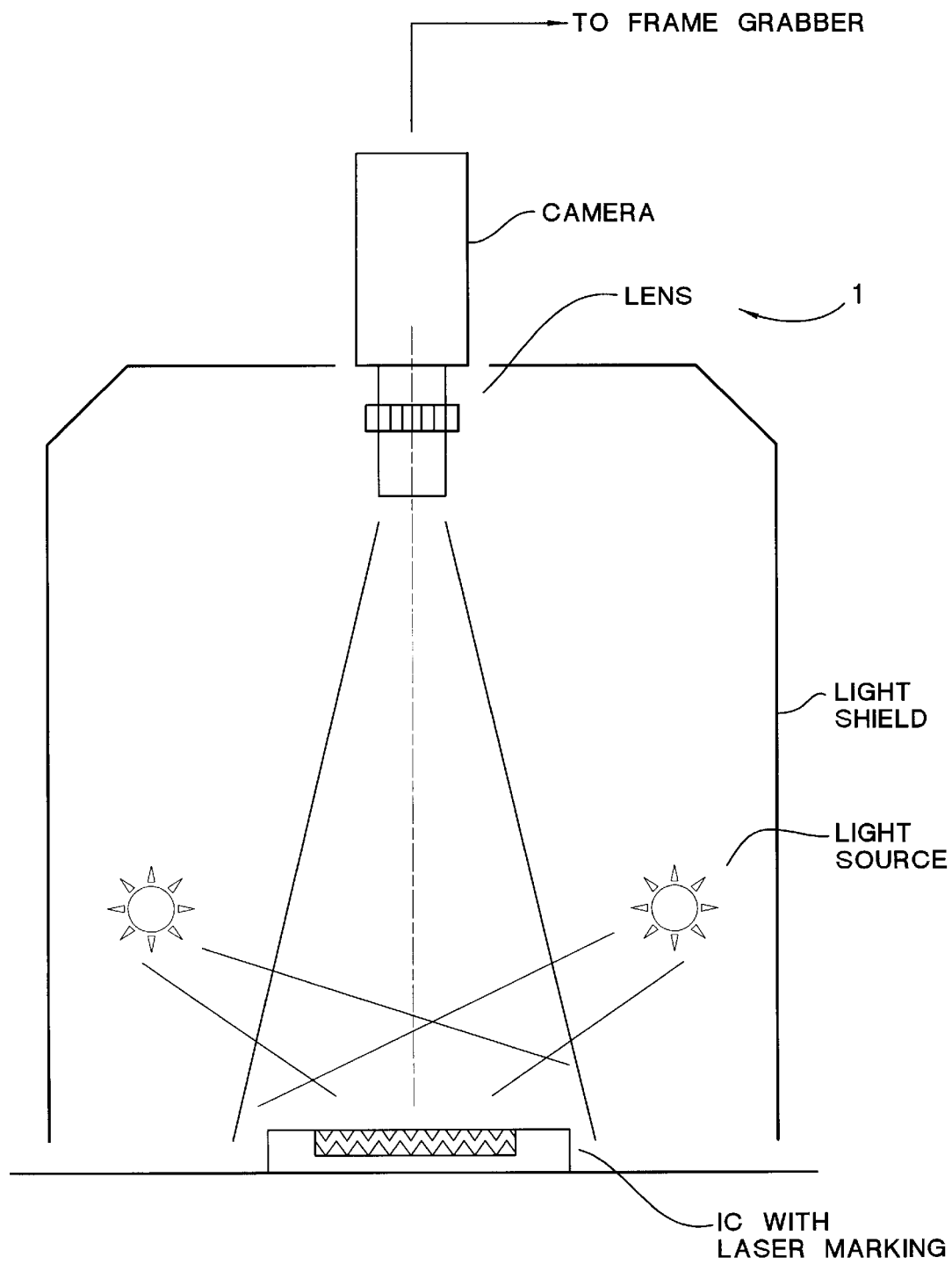

In order to measure the contrast of the laser mark objectively and consistently, a controlled lighting and viewing environment should be established. A specific embodiment of a system for measuring contrast for laser marks according to the present invention is illustrated in FIG. 3A and FIG. 3B. This embodiment includes an image processor system 1, light sources 61. A holder (not shown) is used to hold the object 5 in place. The image processor 1 further includes a video camera 50, lens 51, frame grabber 55, and a processor 57. In general, the video camera 50 includes a high grade CCD (charge coupled device) image sensor 50a. The contrast measurement system is properly enclosed by a light shield 60 to shield off ambient light. The contrast measurement system is illustrated in FIG. 3A and FIG. 3B.

Figure 4:
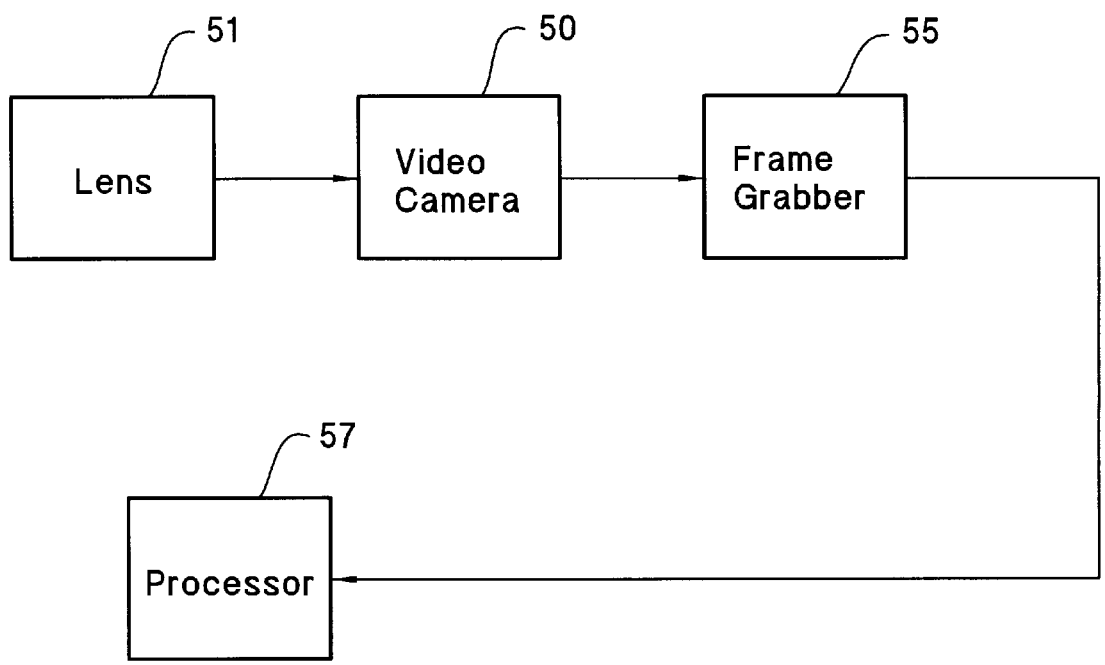

In this specific embodiment, the frame grabber 55 and the video camera 50 of the image processing system 1 are monochromatic. Typically, a 8-bit gray scale representation is used. A typical image processing system 1 is shown in FIG. 4. The lens 51 further has an aperture 51a that is adjustable. An image of the object 5 which is a laser marked IC is focused by the lens and impinged onto the CCD sensor 50a of the video camera 50. The CCD sensor 50a produces an analogue video signal which is fed to the frame grabber 55. The frame grabber 55 digitizes the video signal into 8-bit digital signal which is equivalent to 256 gray level. The digital image is a 2D (two dimensional) array of 8-bit data which can be processed by a computer.

Many variables can affect the final contrast measurement result. Given that the light sources 61 are well controlled, one first adjustable parameter is the lens aperture 51a. The diameter of the lens aperture 51a controls the amount of light that can pass through the lens 51 and be collected by the CCD sensor 50a. The aperture 51a setting is represented by F-number. A large F-number means that the diameter of the aperture 51a is small and hence cut off a large portion of light. A small F-number, on the other hand, will admit more light. The F-number also determines the depth-of-field of the image acquisition system 1. A first step is to ensure that a proper F-number is selected and locked. The amount of light impinged onto the CCD sensor 50a should not be too strong to cause saturation. The light should not be so weak that the signal to noise ratio becomes poor.

Once the F-number of the lens 51 is fixed, the next adjustable parameter is associated with the video camera 50. The video gain of the video camera 50 should be set to a fixed gain level. The video output from the video camera 50 is fed to the frame grabber 55, which has several adjustable parameters. A frame grabber 55 normally has a video amplifier, a sync stripper, and a flash A-to-D converter. The A-to-D converter converts analog signals from the camera into digital signals. The user accessible parameters are gain and offset of the A-to-D converter. The gain and offset for the entire measuring process should be set. The adjustment of the gain and offset of the frame grabber 55 is carried out during the calibration process.

The calibration process can be achieved by the use of a standard gray scale card 30 as the test object. The standard gray scale card 30 has a series of known optical density steps. Such gray scale cards are know in the art and commercially available. One such gray scale card is the KODAK gray scale cards produced by KODAK Co. for photographer. The KODAK gray scale card 30 is used by the present invention as the standard gray scale reference. The KODAK gray scale card 30 is easily available to both the end user and the IC manufacturer. The KODAK gray scale card 30 has a tightly controlled specification and is traceable to ANSI standard. The original purpose of the KODAK gray scale card 30 include the following:

1) Compare the tone values of reflection originals with the tone values of their reproduced image.
2) Compare exposure and processing in a photographic (marking) environment so that changing conditions can be identified, measured and controlled.
3) Balance positive and negative in a color reproduction process that requires the use of masks, separation films, and filters.
4) Determine values for tone-reproduction curves.

The KODAK gray scale card 30 is composed of twenty optical density steps; step aims are 0.10 density increments and relative density values from a nominal "white" of approximately 0.05 to 1.95. Density increments are tightly controlled and will vary only slightly from the nominal density value. Neutrality and uniformity are also tightly controlled. The background approximates an 18% neutral gray to neutralize flare and adjacency effects.

In an illustrative embodiment, the image acquisition system 1 of the present invention is calibrated according to the following steps:

1) Establish the lighting and viewing environment of the contrast measurement system according to the requirement. For the case of measuring the contrast of laser mark, oblique front lighting technique is used.
2) Position the medium gray scale (optical density equals to 0.9) of the KODAK gray scale card 30 in the field of view of the video camera 50.
3) Capture the image of the medium gray scale.
4) Measure the mean intensity of the image of the medium gray scale.
5) Adjust the aperture 51a of the lens 51 such that the intensity of the medium gray scale to be approximately 80 (based on a 8 bit image acquisition system).
6) Position the gray scale with optical density of 0.4 of the reference gray scale card 30 in the field of view of the camera 50.
7) Capture the image and measure the mean intensity of the gray scale of 0.4 optical density.
8) Adjust the gain and offset of the image acquisition system 1 such that the mean intensity of the 0.4 optical density gray scale is close to the upper limit of the image acquisition system 1 but ensuring no intensity saturation. For example, intensity level equals to 250.
9) Position the gray scale with optical density of 1.4 of the KODAK gray scale card in the field of view of the camera.
10) Capture the image and measure the mean intensity of the gray scale of 1.4 optical density.
11) Adjust the gain and offset of the system such that the mean intensity of the 1.4 optical density gray scale is close to the lower limit of the image acquisition system 1. For example, intensity level equals to 25.
12) The parameters of the image acquisition system 1 including the camera lens 51 are now calibrated.

Contrast can be defined as $$\text{Contrast} = (I_{max} - I_{min})/(I_{max} + I_{min}),$$

where $I_{max}$ is the maximum intensity of the region of interest, and $I_{min}$ is the minimum intensity in the region of interest.

Figure 5:
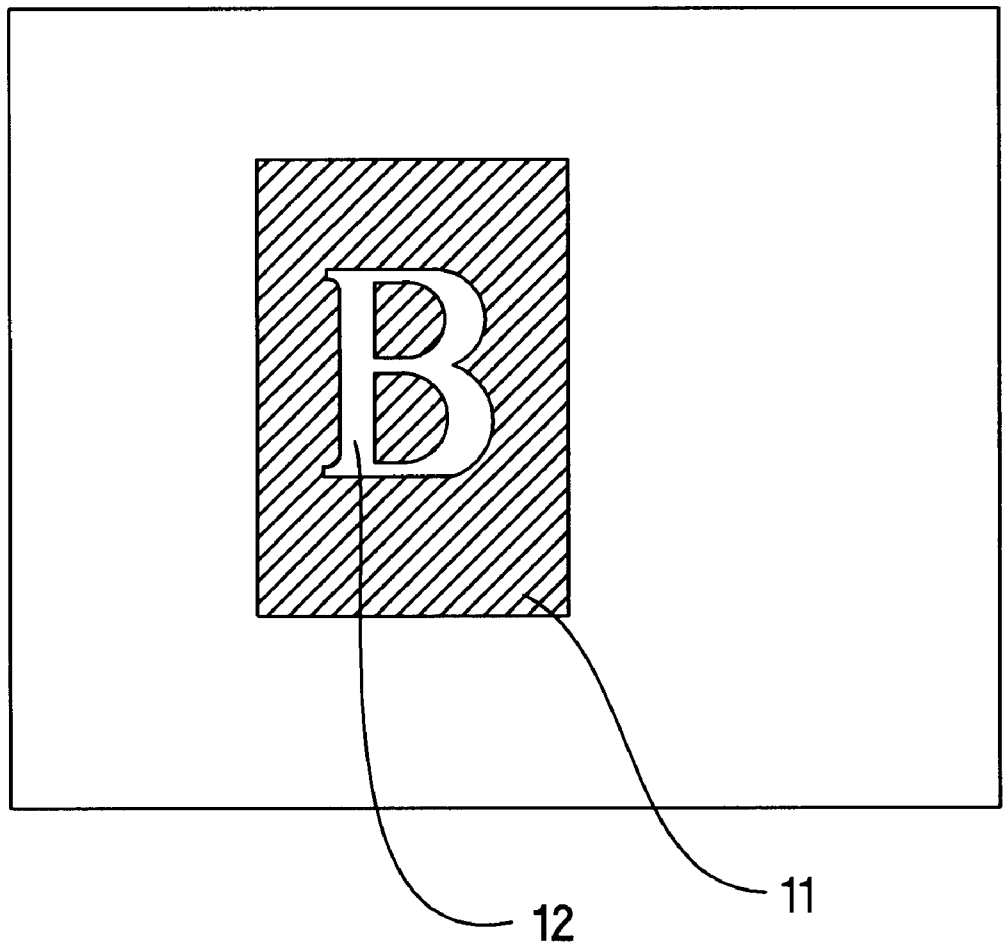
Figure 6:
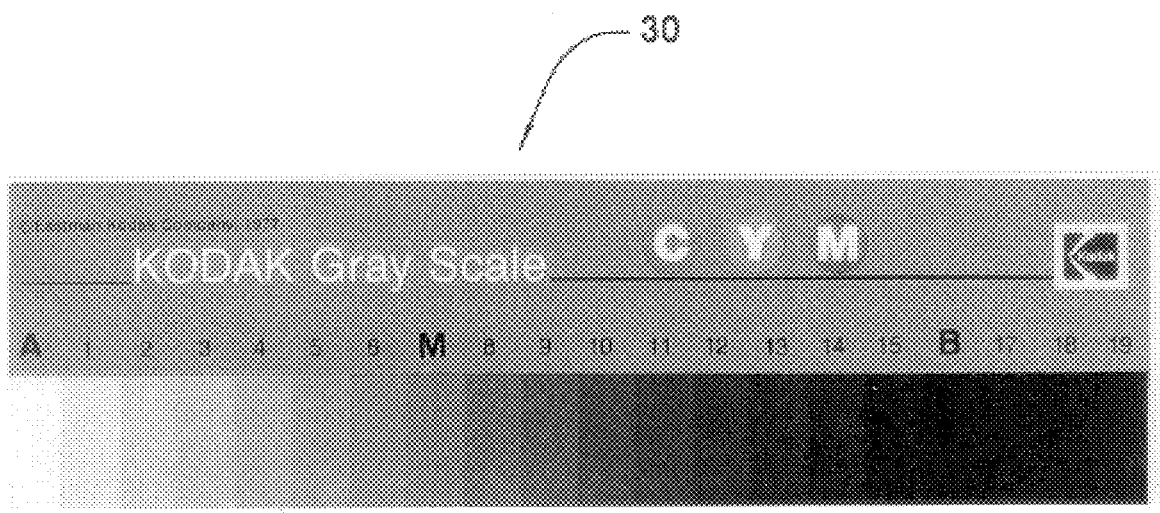

FIG. 5 shows a letter "B" 12 laser marked on a surface 11. Following the above contrast definition, the laser mark contrast is computed by $$\text{Contrast} = (I_M - I_U)/(I_U + I_M),$$

where $I_M$ is the intensity of the laser mark 12 and $I_U$ is the intensity of the background which is the unmarked IC surface 11. It should be noted that the intensity of the background 11 is sampled from the immediate neighborhood of the laser mark 12.

The contrast value is normalized from 0 to 1.0. For example, if $I_U$ is zero while $I_M$ is non-zero, contrast would be equal to 1.0. If $I_M$ is equal to $I_U$, then contrast is 0.

According to the present invention, an optical system such as one described above (e.g., one shown in FIG. 3) can be used to measure the intensity values $I_U$ and $I_M$ and a processor (e.g., a computer such as a desk-top personal computer, a minicomputer, or a mainframe computer) can be used to calculate the contrast according the contrast equation above. A computer program can be written to implement the algorithm according to the equation in the computer. The result of the calculation can then be communicated to a typical output units to a user. For example, the result can be broadcast in a CRT monitor display, printer, relayed to another computer, stored in a storage device such as a hard disk, floppy disk, tape, compact disk, and the like. Furthermore, the algorithm can be stored in an article of manufacture, such as a computer, disks, and the like such as the above-mentioned.

Although the above equation can be used to calculate contrast of laser marks, according the present invention, a more preferred way of calculation can be used. One reason is that the above contrast measurement is non-linear and there is no objective way of communicating the contrast value.

In another embodiment, the present invention provides a new way of computing contrast after the image acquisition system has been calibrated according to the above mentioned procedure.

$$\text{Contrast\_new} = |\text{Log}(I_M) - \text{Log}(I_U)|$$

Contrast_new is also a normalized value with a scale of 0.0 to 1.0. Using the KODAK gray scale card 30, the user can simply specify an acceptable contrast value based on the difference in the density steps provided. The measured contrast value (Contrast—new) will then be compared with this user defined value to determine whether the laser mark contrast is acceptable or not. In other words, by this technique, the present invention uses video imaging to measure the optical density of the laser marks.

According to the present invention, in order to measure a laser mark contrast, the system first segments the laser mark 12 from the background 11 and further extracts their respective intensity values. The uniformity of the marked area and that of the unmarked areas are computed as well. Due to the variations in the laser beam energy, the amount of material removed from different areas may be different and hence the laser mark will appear uneven. The present invention also measures the evenness of the laser mark in addition to the contrast itself.

In summary, the present invention provides an improved technique for inspecting contrast of a laser mark (e.g., a logo). An illustrative procedure is as follows:

Measure the optical density of a portion of the laser mark 12 and the unmarked surface 11 under a controlled illumination environment;

Compute the contrast of the laser mark based on the optical density measurement;

Compare the contrast of the portion of the laser mark with a pre-defined reference which is preferably the KODAK gray scale card 30 to determine whether the contrast is acceptable or not. Preferably, the comparison is based on the contrast calculation using the equation:

$$\text{Con} = |\text{Log}(I_M) - \text{Log}(I_U)|.$$

Similarly compute the contrasts of other portions of the laser mark based on the optical density measurements of the other portions of the laser mark and the unmarked surface 11.

Compute a deviation of the contrasts.

Compare the deviation of the contrasts with a pre-defined acceptable value. If the deviation falls within the pre-defined acceptable value, the laser mark is deemed acceptable.

What is claimed is:

1. A method for establishing the quality of a laser mark applied to a surface comprising the steps of:

illuminating a reference gray scale;

obtaining equivalent intensity readings from light reflected off gray level steps on the reference gray scale whose optical densities are known to establish a quality reference;

illuminating the laser mark; and obtaining a first intensity reading ($I_M$) from light reflected off a portion of the laser mark to derive an absolute measure of quality of the laser mark based on the quality reference.

2. A laser marking quality establishing method according to claim 1, further comprising the steps of:

illuminating an unmarked surface adjacent to the laser mark when illuminating the laser mark;

obtaining a second intensity reading ($I_U$) from light reflected off the unmarked adjacent surface; and deriving a measure of contrast from the first and second intensity readings to obtain a relative measure of quality based on the quality reference.

3. A laser marking quality establishing method according to claim 2, further comprising the steps of:

deriving measurements of contrast for different portions of the laser mark; and calculating a deviation of contrast from the measurements of contrast for establishing a uniformity measure of the laser mark.

4. A laser marking quality establishing method according to claim 2, wherein the measure of contrast (Con) is obtained according to the equation:

$$\text{Con} = |\text{Log}(I_M) - \text{Log}(I_U)|$$

5. A laser marking quality establishing method according to claim 1, wherein the reference gray scale is a standards-based gray scale.

6. A laser marking quality establishing method according to claim 5, wherein the standards-based gray scale is a KODAK gray scale.

7. A system for establishing the quality of a laser mark on a surface comprising:

a light source for illuminating a reference gray scale and the laser mark;

an image sensor for determining the intensity of light reflected off the reference gray scale and the laser mark; and a processor for capturing values corresponding to the intensity of light reflected off the reference gray scale for establishing a quality reference and for capturing a value corresponding to the laser mark ($I_M$) for deriving an absolute measure of quality based on the quality reference.

8. A system according to claim 7, wherein the image sensor further determines the intensity of light reflected from an unmarked surface adjacent to the laser mark and wherein the processor captures a value corresponding to the intensity of light reflected off the unmarked surface ($I_U$) for calculating a measure of contrast from the values corresponding to the intensity of light reflected off the laser mark and the unmarked surface adjacent to the laser mark.

9. A system according to claim 8, wherein the processor derives measurements of contrast for several portions of the laser mark and calculates a deviation of contrast from the measurements of contrast to establish a uniformity measure of the laser mark.

10. A system according to claim 8, wherein the processor calculates the measure of contrast (Con) according to the equation:

$$\mathrm{Con} = |\mathrm{Log}(I_M) - \mathrm{Log}(I_U)|$$

11. A system according to claim 7, wherein the reference gray scale is a standards-based gray scale.

12. A system according to claim 11, wherein the standards-based gray scale is a KODAK gray scale.

13. A system according to claim 7, wherein the image sensor comprises a photoelectric conversion element having an adjustable light receiving aperture for sensing light intensity and wherein the system further comprises an analog to digital converter to convert output from the image sensor from an analog to a digital signal.

14. A program storage device readable by a processor in a system, tangibly embodying a program of instructions, executable by the processor to perform the method steps for establishing the quality of a laser mark applied to a surface, the method comprising the steps of:

illuminating a reference gray scale;

obtaining equivalent intensity readings from light reflected off marks on the reference gray scale whose optical densities are known to establish a quality reference;

illuminating the laser mark; and obtaining a first intensity reading ($I_M$) from light reflected off a portion of the laser mark to derive an absolute measure of quality of the laser mark based on the quality reference.

* * * * *